US00PP20339P2

(12) United States Plant Patent
Coakley

(10) Patent No.: US PP20,339 P2
(45) Date of Patent: Sep. 22, 2009

(54) ***DELPHINIUM* PLANT NAMED 'CRYSTAL DELIGHT'**

(50) Latin Name: ***Delphinium* hybrid**
Varietal Denomination: Crystal Delight

(76) Inventor: Tony Coakley, 33 Rosebank Avenue, Blantyre, Glasgow (GB), G72 9BB ( * ) Notice: Subject to any disclaimer, the term of this patent is extended or adjusted under 35 U.S.C. 154(b) by 0 days.

(21) Appl. No.: 12/221,428

(22) Filed: Aug. 2, 2008

(51) Int. Cl.
*A01H 5/00* (2006.01)

(52) U.S. Cl. ..... Plt./423

(58) Field of Classification Search ..... Plt./423
See application file for complete search history.

*Primary Examiner*—Annette H Para

(57) ABSTRACT

A new and distinct *Delphinium* hybrid cultivar named 'Crystal Delight' is disclosed, characterized by an upright plant habit, vigorous growth and lavender and green flowers with a large quantity of petals. The new cultivar produces strong flower stems, freely and continuously flowering from early through late Summer. The new variety is a *Delphinium* hybrid, suitable for garden or outdoor container use.

1 Drawing Sheet

Figure 1:
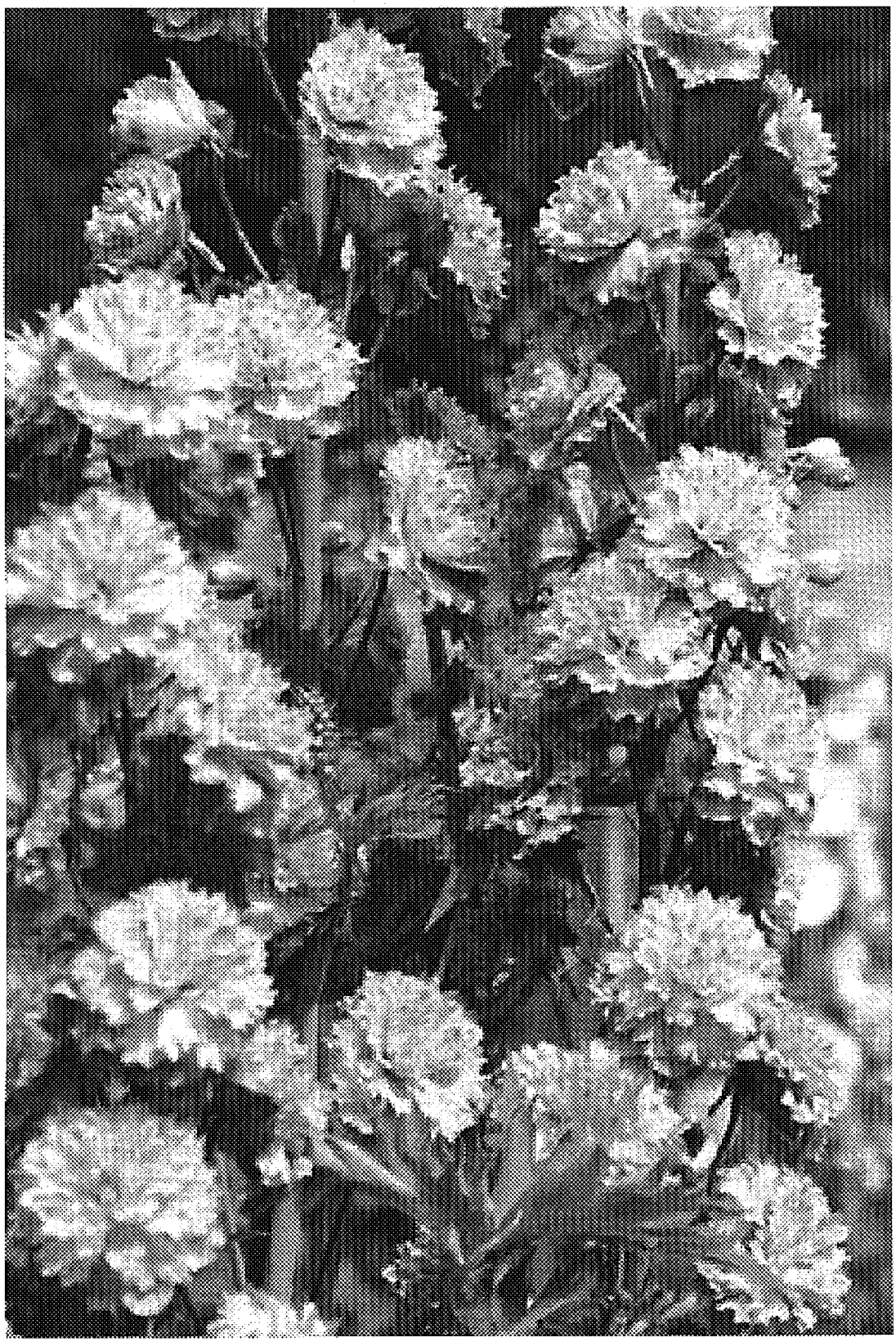

Latin name of the genus and species: *Delphinium* hybrid. Variety denomination: 'CRYSTAL DELIGHT'.

BACKGROUND OF THE INVENTION

The new variety was discovered, by the inventor, as the result of a hand crossed, planned breeding program in Scotland. The parent varieties are both unnamed, undistributed proprietary seedlings. The discovery of the new variety was made by the inventor, Tony Coakley in August 2001 in a cultivated field of *Delphiniums* in Glasgow, Scotland.

Asexual reproduction of the new cultivar 'Crystal Delight' by tissue culture was performed in the Netherlands following selection and has shown that the unique features of this cultivar are stable and reproduced true to type in successive generations.

SUMMARY OF THE INVENTION

The cultivar 'Crystal Delight' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Crystal Delight' These characteristics in combination distinguish 'Crystal Delight' as a new and distinct *Delphinium* cultivar:

1. Upright plant habit.
2. Vigorous growth habit.
3. Strong flower stem.
4. Freely and continuous flowering habit.
5. Increased number of petals.
6. Unique flower color combination of lavender and green.

Plants of the new cultivar 'Crystal Delight' are similar to plants of the seed parent variety, an unnamed *Delphinium* hybrid in most horticultural characteristics; however, flowers of the new variety have more petals, and a stronger, more consistent color.

Plants of the new cultivar 'Crystal Delight' are similar to plants of the pollen parent variety, an unnamed *Delphinium* hybrid in most horticultural characteristics; however, flowers of the new variety have more petals, and a stronger, more consistent color.

The inventor is unaware of similar commercial varieties for comparison to 'Crystal Delight.' The strong flowering stems, unique flower coloration and increased petal count make the new cultivar unlike other *Delphiniums* in the trade.

BRIEF DESCRIPTION OF THE PHOTOGRAPH

The accompanying photograph in FIG. 1 illustrates in full color a typical plant of 'Crystal Delight' grown outdoors in Scotland. The pot size is a 1 liter container. The plant shown is approximately 9 months. The photograph was taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart except where general terms of ordinary dictionary significance are used. The following observations and measurements describe 'Crystal Delight' plants grown outdoors in the Scotland from Winter to Summer. The growing temperature ranged from 5° C. to 17° C. at night to 14° C. to 28° C. during the day. Measurements and numerical values represent averages of typical flowering types.

Botanical classification: *Delphinium* hybrid cultivar 'CRYSTAL DELIGHT.'

PROPAGATION

Time to rooting: About 4 to 5 weeks at approximately 10° C.
Root description: Fine, fibrous and fleshy roots.

PLANT

Growth habit: Upright herbaceous perennial.

Height: Approximately 110 cm.

Blooming period: Naturally blooming continuously from early through late Summer.

Plant spread: Approximately 60 cm.

Growth rate: Vigorous.

Branching characteristics: Very little branching.

Length of lateral branches: Approximately 60 cm.

Diameter of lateral branches: Approximately 2.0 cm.

Quantity of lateral branches: Approximately 2 to 3.

Texture of lateral branches: Smooth, non-pubescent.

Color of lateral branches: Near RHS Green 143B.

Aspect: Approximately 15 to 25° Angle.

Number of leaves per lateral branch: Approximately 37.

Age of plant described: Approximately 9 months from a rooted tissue culture liner.

FOLIAGE

Leaf:

*Arrangement.*—Rosette at plant base and alternate along flowering stems.

*Average length.*—Approximately 15 cm.

*Average width.*—Approximately 18 cm.

*Shape of blade.*—Palmately lobed; Symmetrical.

*Apex.*—Acute to acuminate.

*Base.*—Reniform to hastate.

*Attachment.*—Stalked.

*Margin.*—Incised.

*Texture of top surface.*—Smooth.

*Texture of bottom surface.*—Smooth.

*Color.*—Upper side: Near R.H.S. Green 137A. Under side: Near Green 138B.

*Venation.*—Type: Pinnate. Venation color upper side: Near Green 137A. Venation color under side: Near Green 138B.

Petiole:

*Length.*—Approximately 13 cm.

*Diameter.*—Approximately 0.4 cm.

*Coloration.*—Near RHS Green 138B.

*Texture.*—Smooth.

FLOWER

Bloom period: Typically flowering continuously from early through late Summer.

Bud:

*Bud shape.*—Orbicular.

*Bud length.*—Approximately 2.5 cm.

*Bud diameter.*—Approximately 2.5 cm.

*Bud color.*—Near RHS Yellow-Green 144D.

Inflorescence:

*Form.*—Numerous multi-petaled flowers arranged on a raceme.

*Length of flowering stem.*—Approximately 50 cm.

*Diameter of flowering stem.*—Approximately 14 cm.

Flower:

*Quantity of individual flowers per flowering stem.*—About 50.

*Diameter of individual flower.*—Approximately 6.0 cm.

*Depth of individual flower.*—Approximately 2.5 cm.

*Fragrance.*—None.

*Persistence.*—Flowers persist.

Petals/petaloids:

*Arrangement.*—Whorled.

*Aspect/orientation.*—Flat outward to slightly downward, approximately 5° angle.

*Shape.*—Oblong.

*Quantity.*—Approximately 43.

*Length.*—Approximately 3.0 cm.

*Width.*—Approximately 1.2 cm.

*Apex shape.*—Dentate.

*Base.*—Roughly obtuse.

*Margin.*—Entire.

*Texture.*—Slightly rugose.

Color:

*Upper surface at first opening.*—Near RHS Yellow-Green 144A and Purple 76A.

*Upper surface at maturity.*—Near RHS Purple 76A with Yellow-Green 144A and White 155A.

*Upper surface at fading.*—Not fading, same as mature coloration.

*Under surface at first opening.*—Near RHS Yellow-Green 144A and Purple 76A.

*Under surface at maturity.*—Near RHS Purple 76A with Yellow-Green 144A and White 155A.

*Under surface at fading.*—Not fading, same as mature coloration.

Sepals:

*Shape.*—Oblong.

*Quantity.*—Approximately 15.

*Length.*—Approximately 1.8 cm.

*Width.*—Approximately 1.2 cm.

*Apex shape.*—Dentate.

*Color.*—Near RHS Yellow-Green 144A and White 155C.

*Margin.*—Entire.

*Texture.*—Smooth.

REPRODUCTIVE ORGANS

All organs are fragmented due to the amount of petals, making the cultivar sterile.

OTHER CHARACTERISTICS

Disease resistance: Neither resistance nor susceptibility to diseases or pests has been observed in this variety.

Drought tolerance and temperature tolerance: Extremely hardy perennial. Hardy to −20 ° C. Upper temperature tolerance unknown. No tolerance for drought Fruit/seed production: Cultivar is sterile, no fruit or seed produced.

What is claimed is:

1. A new and distinct cultivar of *Delphinium* plant named 'Crystal Delight' as herein illustrated and described.

* * * * *